United States Patent [19]
Bell et al.

[11] Patent Number: 4,828,495
[45] Date of Patent: May 9, 1989

[54] SINTERED ALLOY DENTAL PROSTHETIC DEVICES AND METHOD

[75] Inventors: A. Milton Bell, Cresskill; Murray G. Gamberg, Manalapan; Ronald Kurzeja, Bridgewater, all of N.J.

[73] Assignee: Denpac Corp., Hackensack, N.J.

[21] Appl. No.: 923,898

[22] Filed: Oct. 28, 1986

Related U.S. Application Data

[63] Continuation-in-part of Ser. No. 674,966, Nov. 26, 1984, Pat. No. 4,671,770, and a continuation-in-part of Ser. No. 622,997, Jun. 21, 1984, Pat. No. 4,661,071, which is a continuation-in-part of Ser. No. 596,314, Apr. 2, 1984, abandoned.

[51] Int. Cl.⁴ .......................................... A61C 13/00
[52] U.S. Cl. ............................. 433/200.1; 433/201.1; 623/16
[58] Field of Search .................. 433/200.1, 222.1, 223, 433/207, 213, 201.1; 264/16, 19; 128/92 C; 623/16

[56] References Cited

U.S. PATENT DOCUMENTS

| | | | |
|---|---|---|---|
| 2,106,809 | 8/1938 | Prange | 433/200.1 |
| 2,206,502 | 7/1940 | Heiligman | 166/35 |
| 2,263,586 | 11/1941 | Neiman | 106/38.3 |
| 3,450,545 | 6/1969 | Ballard | 106/1.13 |
| 3,464,837 | 9/1969 | McLeaon et al. | 106/35 |
| 3,541,688 | 11/1970 | McLean et al. | 433/208 |
| 3,549,393 | 12/1970 | Elarde | 501/154 |
| 3,647,488 | 3/1972 | Brigham et al. | 264/16 |
| 3,649,733 | 3/1972 | Brigham | 264/63 |
| 3,758,317 | 9/1973 | Moore et al. | 501/128 |
| 3,761,728 | 9/1973 | Kochavi | 433/218 |
| 3,786,565 | 1/1974 | Jarrault | 433/200.1 |
| 3,920,578 | 11/1975 | Yates | 106/38.3 |
| 3,934,348 | 1/1976 | Janjic | 433/223 |
| 3,987,545 | 10/1976 | Kennedy | 433/36 |
| 4,069,057 | 1/1978 | Kamei et al. | 501/128 |
| 4,104,798 | 8/1978 | Takahashi et al. | 433/222.1 |
| 4,114,272 | 9/1978 | Saragossi | 433/207 |
| 4,172,867 | 10/1979 | Devault | 264/16 |
| 4,181,757 | 1/1980 | Youdelis | 427/229 |
| 4,235,630 | 11/1980 | Baby | 419/12 |
| 4,243,412 | 1/1981 | Tandon | 420/445 |
| 4,249,943 | 2/1981 | Mohammed | 420/455 |
| 4,265,669 | 5/1981 | Starling | 166/35 |
| 4,321,042 | 3/1952 | Scheicher | 433/201.1 |
| 4,358,271 | 11/1982 | Sperner et al. | 433/201 |
| 4,369,068 | 1/1983 | Haussett et al. | 433/200.1 |
| 4,386,962 | 6/1983 | Walker | 433/222 |
| 4,426,404 | 1/1984 | Shoher et al. | 433/223 |
| 4,431,451 | 2/1984 | Mabie et al. | 433/202 |
| 4,433,958 | 2/1984 | Fellman et al. | 433/199 |
| 4,457,709 | 7/1984 | Moore | 433/74 |
| 4,461,618 | 7/1984 | DeLuca et al. | 433/207 |
| 4,468,251 | 8/1984 | Hausselt et al. | 433/219 |
| 4,501,613 | 2/1985 | Motsumoto | 75/228 |
| 4,508,835 | 4/1985 | Kaniuk et al. | 501/128 |
| 4,527,979 | 7/1985 | McLean et al. | 433/9 |
| 4,530,722 | 7/1985 | Moore et al. | 106/38.3 |
| 4,562,882 | 1/1986 | Alleluia | 433/200.1 |
| 4,585,417 | 4/1986 | Sozio et al. | 433/202.1 |
| 4,689,197 | 8/1987 | Groll et al. | 264/16 |

FOREIGN PATENT DOCUMENTS

| | | | |
|---|---|---|---|
| 238088 | 11/1969 | U.S.S.R. | 433/213 |
| 1097330 | 6/1984 | U.S.S.R. | 433/213 |

OTHER PUBLICATIONS

Ceramic Industry vol. 120(1) Jan. 1983 "Kyanite" p. 92, Mullite, pp. 161.

Phillips, R. W. *Skinner's Science of Dental Materials*. 8th ed. 1982, W. B. Saunders Co., pp. 406–410, 550–556 Ceramic Industry, vol. 120 (1) Jan. 1983 "Spadumene", p. 122.

*Primary Examiner*—John J. Wilson
*Attorney, Agent, or Firm*—Lackenbach Siegel Marzullo & Aronson

[57] ABSTRACT

This invention relates to biomechanical devices comprising a liquid sinterable metallic alloy, characterized by a multiphase, composite microstructure of isolated spherical grains approximately 50 microns in diameter distributed in an essentially nonporous matrix. The dental prosthetic devices include full-cast crowns, copings, pontics, inlays, onlays, and bridges. Other devices include reconstructive and orthopedic pieces. A method for fabricating a dental prosthetic device is also recited.

44 Claims, 3 Drawing Sheets

FIG. 1 PROCESS FOR A SINGLE COPING

FIG. 2 PROCESS FOR A THREE-UNIT BRIDGE

FIG. 4

SINTERED ALLOY DENTAL PROSTHETIC DEVICES AND METHOD

RELATED U.S. PATENT APPLICATIONS

This application is a continuation-in-part of Ser. No. 674,966 filed Nov. 26, 1984, now U.S. Pat. No. 4,671,770, and also is a continuation-in-part of Ser. No. 622,997 filed June 21, 1984, now U.S. Pat. No. 4,661,071 which is a continuation-in-part of Ser. No. 596,314 filed Apr. 2, 1984, now abandoned.

FIELD OF THE INVENTION

This invention relates to fixed and removable dental prosthetic and similar biomechanical devices such as crowns, inlays, onlays, pontics, bridges and the like, made of sintered metal alloys. Other precise sintered alloy pieces may also be provided, such as bone pins, reconstructive bone parts, and other orthopedic devices.

BACKGROUND OF THE INVENTION

This invention relates to making and using sintered metal copings, bridges, onlays, inlays, crowns, and the like which have superor physical properties and which show superior dimensional fit, separation, and alignment than the usual cast metal prosthetic devices. Other short run, biomechanical devices may also be constructed by these same techniques.

Hitherto metallic dental prosthetic devices have been cast by processes such as investment casting, the "lost wax" process, to yield a homogeneous microstructure of one fine phase or multiphase fine grain microstructures with appreciable porosity. The microstructure of the porosity of cast metals is irregular and may even show channels. Often the porosity is spherical in the general range of one micron. The level of porosity is about one percent.

The liquid phase sintered dental devices of the present invention exhibit under an optical microscope a composite structure. In this novel structure discontinuous grains are dispersed in a continuous matrix. Even if the starting material of the sintered alloy is of uniform composition, the heterogeneous two-phase product may show higher melting grains of one composition in a lower melting matrix of another composition. This disparity in composition arises from the fact that the sintering is carried out at a temperature between that of the liquidus and solidus temperatures.

Making and using the sintered powdered alloy devices, having multiple units of this invention, obviates the soldering together of single units, which leads to porosity and inferior alignment, and soldering difficulties caused hitherto by oxidation of the metallic surfaces.

Cast, full-coverage dental restorations inherently result in unsatisfactory seating. There are so many steps to the casting process that multiple units are not well aligned because of the many opportunities for dimensional errors. Thus in the classical casting of dental devices the margins of the casting do not generally coincide with the finish line of the prepared tooth. This is especially so for castings of non-precious metals, because there is excessive contraction of the alloy as it cools from the molten state to the solid state. The remedies are to grind away the interferences in the newly cast restoration and grind the opposing natural tooth to permit the jaws of the patient to close normally. Or when working the cast bridges, the dental technician employs multiple layers of spacer materials on the dies of the prepared teeth resulting in a very loose fit conpensated for by excessive cement.

Until this invention practitioners did not match the physical expansion, the thermal expansion, and variations in both of the die materials with the thermal expansion of the sintering alloy to achieve a fit in dental devices at room temperature consistently less than 50 microns.

Furthermore, until this invention no one has used two different die materials: an abutment die material to make a preform for the copings or crowns and a base die material to join the various segments of the bridge, so that a fit of less than 50 microns results when multitooth dental devices are made from die materials with different physical and thermal expansions.

The conventional method for making a dental preform relies on the "lost wax" technique, which involves casting molten metal into a hollow ceramic investment material shaped around an original wax model.

The wax model is formed to fit precisely a die which is a replica of the prepared surface of the teeth made by the dentist from a dental impression. Therefore, to make a cast alloy or porcelain dental device, such as a full cast crown, veneer crown, coping, pontic, inlay, onlay, or bridge by the lost wax process involves six steps between seven entities: prepared tooth, impression, die, wax model, hollow investment, metal replica, dental device. Trying to accomplish this six-stage process with good dental "fit" leads to variable results ranging from +200 microns or more to a negative fit which cannot be seated upon the original die or prepared tooth.

In general, the following steps are customary in the lost wax process:

(1) The dentist prepares a tooth or teeth to be restored in different ways according to which prosthodontic device is to be used: crown, bridge, splint, or fixed partial denture.

(2) The dentist then makes an impression of the prepared tooth or teeth in an accurate manner. From this impression a model is made. With this model or replica the dentist supplies an accurate duplication of the patient's opposing arch and a bite registration in what is known as centric relation. Thus a highly accurate duplication of the prepared teeth on which the prosthesis is to be fabricated and the maxillo-mandibular relationship is provided in model form. Even in the restoration of a single crown, the dentist provides the technician with an accurate duplication of the adjacent teeth, as well as the opposing teeth, in order to permit the building of contact points and occluding contact point in both the rest position of the jaws as well as in masticatory movement.

(3) Since the final restoration of a crown or bridge must harmonize with the patient's dentition in appearance as well as function, a precise model permits fabrication of a wax pattern comforming to a specific design for a dental device.

(4) The finished wax pattern is sprued, then removed from the die, and connected to a sprue former using a precise system of waxes to attempt later complete casting of the metal. Since the wax pattern is removed from the die to be invested, this is considered an indirect fabrication technique. It is important to note that discrepancies may be introduced in an indirect technique due to distortion of the wax pattern during its removal from the die. The wax may distort in the investing process. The wax and investment materials may undergo contraction or expansion due to temperature changes during setting and burn-out of the investment and casting, and solidification of the molten metal during the cooling cycle.

(5) The sprued wax pattern is then invested in a high heat material, depending upon the type of metal being cast.

(6) The invested wax pattern, when set (cured), is placed in a burn-out oven for a period of one and a half hours or more, depending upon the technique and metal being cast. Temperatures in the burn-out oven may range from about 650° C. to about 1000° C., in one or more heat stages to insure maximum expansion of the investment. This expansion during the heating cycle varies and may be a cause of an improper fit of the final restoration, if not properly controlled. The burn-out procedure not only expands the investment in preparation for the casting of the molten metal, but is essential for elimination of all the wax, thus leaving a void in the investment material that is a mould of the eliminated wax pattern.

(7) A casting ring is employed to contain the investment material around the wax pattern. Spacers in the casting ring are used to permit expansion of the investment during the heating stage. This may lead to an imprecise fit of the final casting. Some investment materials employ a plastic or paper ring for forming and containing the investment material. The plastic or paper is either burned-off during the burn-out state or removed after the investment has set. This allows for maximum expansion of the investment during the heating stage. The actual casting is made by placing the investment, which was formed by some kind of device, into some type of castng apparatus after the burn-out stage. This permits melting of the desired metal at the required temperature. The molten metal is then forced into the mould in the hot investment either by centrifugal force, pressure, or vacuum. There are different types of equipment for these various methods of making a casting. Once the cast has been completed, the metal and investment material are allowed to cool.

(8) The casting must be recovered from the investment material by breaking it out from the investment. The casting is then cleaned off.

(9) The sprues are then cut off the crown, bridge or pontic and smoothed down. The casting must be then fitted back upon the original die. If the technician utilizes a gypsum die, it may be difficult to seat the casting on the model without scraping or chipping the die. The ultimate fit on the tooth is therefore complicated for the dentist.

Miscasts and incomplete casting which fail to reproduce fine details of the original wax pattern, or poor fit of the casting due to contraction and expansion of the wax and investment material are not uncommon. This may require repeating the entire procedure, if the casting cannot be properly seated on the die or the prepared tooth of the patient.

While dental bridges can either be cast in one piece or assembled from individual units, a more accurate fit is assured by assembly of the units of the bridge or splint from an index impression taken of the units seated in the mouth. This insures complete placement of the device made from the castings upon the individually prepared teeth. This technique has been widely employed for many years, utilizing precious metal alloys which are relatively simple to solder. The non-precious metal alloys employed today are more difficult to solder or braze due to formation of oxide layers on their surfaces when subjected to high temperatures. This had led the dentist to prescribe casting multiple unit bridges and splints in one piece to eliminate the necessity for soldering. There is much question regarding accuracy of fit of such long-span prostheses cast as one device.

These long, labor-intensive techniques of the prior art are costly as well as time-consuming, and often provide a questionable or inaccurate fit.

In the patent literature various ceramic, metallic, and ceramo-metallic materials have been employed in attempts to improve crowns and bridges. Such materials are disclosed in:

| U.S. Pat. No. | Patentee | Granted |
| --- | --- | --- |
| 4,243,412 | Tandon | Jan. 6, 1981 |
| 4,249,943 | Mohammed, et al. | Feb. 10, 1981 |
| 4,265,669 | Starling et al. | May 5, 1981 |
| 2,206,502 | Heiligman | Jul. 2, 1940 |
| 3,649,732 | Brigham et al. | Mar. 14, 1972 |
| 4,321,042 | Scheicher | Mar. 23, 1982 |
| 2,106,809 | Prange et al. | Feb. 1, 1938 |
| 3,450,545 | Ballard et al. | Jun. 17, 1969 |
| 3,786,565 | Jarrault | Jan. 22, 1974 |

| U.S. Pat. No. | Patentee | Granted |
| --- | --- | --- |
| 4,426,404 | Shoher et al. | Jan. 17, 1984 |
| 4,562,882 | Alleluia | Jan. 7, 1986 |
| 2,263,586 | Neiman | Nov. 25, 1941 |
| 4,358,271 | Sperner et al. | Nov. 9, 1982 |
| 3,934,348 | Janjic | Jan. 27, 1976 |
| 3,761,728 | Kochani | Sept. 25, 1973 |
| 4,431,451 | Mabie et al. | Feb. 14, 1984 |
| 4,104,798 | Takahashi et al. | Aug. 8, 1978 |
| 3,541,688 | McLean et al. | Nov. 24, 1970 |
| 3,464,837 | McLean et al. | Sept. 2, 1969 |
| 4,181,757 | Youdelis | Jan. 1, 1980 |
| 4,468,251 | Hausselt et al. | Aug. 28, 1984 |
| 4,433,958 | Fellman et al. | Feb. 28, 1984 |
| 4,527,979 | McLean et al. | Jul. 9, 1985 |
| 4,172,867 | Davault | Oct. 30, 1979 |
| 4,369,068 | Hausselt et al. | Jan. 18, 1983 |
| 4,457,709 | Moore | Jul. 3, 1984 |
| 4,585,417 | Sozio et al. | Apr. 29, 1986 |

SUMMARY OF THE INVENTION

The essence of the present invention is a dental prosthetic device made from a liquid-phase, sintered alloy characterized by a multiphase, composite microstructure and low, isolated, spherical porosity. The porosity is about 0.5 percent in the form of isolated spherical pores less than ten micrometers. The grain structure comprises isolated grains of from about 20 microns to about 80 microns averaging 50 microns in diameter dispersed in a continuous matrix. The grains and matrix may have different elemental compositions even if they arise from the same alloy.

Another aspect of the present invention is the use of two kinds of ceramic, siliceous, die material in the making of metallic dental prosthetic devices. Once is an abutment die material having a thermal expansion between ambient and 600° C. of about 0.01 mm/mm (0.008 to 0.015 mm/mm) and a physical expansion of about zero to 0.03 mm/mm. The other siliceous base die material has a lower thermal expansion (0.004 to 0.015 mm/mm) and a physical expansion of about zero.

Other biomechanical devices may similarly be provided, such as bone pins, reconstructive bone parts, and other orthopedic devices.

In conjunction with these two die materials one employs a powdered, sinterable, alloy with a thermal expansion coefficient of about 0.0008 mm/mm (0.004 to 0.015 mm/mm) between ambient and 600° C. The abutment die has a positive physical expansion. The abutment die material must have a positive physical expansion so that there is a proper fit of the dental device onto the prepared tooth. The abutment die has a larger thermal expansion than the alloy between ambient and 700° C. to give a good "separation" for the dental device.

The multitooth devices show good "alignment" between the various segments of the metallic device, ensured by zero physical expansion and thermal expansion equal to the alloy between ambient and 700° C. of the base die material between the abutments.

Surprisingly, dental prosthetic devices for a single tooth such as a single crown or for several vicinal teeth such as a bridge may be made by the following method, which gives a "fit" between the prosthetic device and the prepared dental surface of less than 50 microns:

(a) forming an impression of the prepared dental surface;
(b) mixing a siliceous abutment die material having a thermal expansion between room temperature and 600° C. greater than that of the alloy of step (f) between room temperature and 600° C. that is from about 0.008 mm/mm to 0.015 mm/mm and a physical expansion between zero and about 0.03 mm/mm;
(c) filling the impression with the abutment die material to form a die preform;
(d) separating the preform from the impression;
(e) firing the abutment die material at a temperature below 1500° C. to form a solid die;
(f) metallizing the die material surface;
(g) covering the die surface with a powdered metal alloy having an expansion coefficient between room temperature and 600° C. between 0.004 mm/mm and 0.015 mm/mm;
(h) firing the alloy/die composite under vacuum at a temperature between 900° C. and 1400° C.

For a multitooth device such as a bridge, two die materials, abutment and base, with tailored thermal and physical expansions are employed, the former for the coping sections and the latter for attaching the coping sections, so that the components of the bridge fit the prepared tooth within 50 microns positive without any cracks or strains, and the bridge has true "alignment" in order to allow proper seating by complete covering of the margins of the prepared tooth.

The preferred die materials are proper mixtures of alpha-quartz, alpha-cristobalite, zirconium silicate (zircon), magnesium oxide, monoammonium dihydrogen phosphate, and colloidal silica. The preferred alloy contains about 80% palladium.

DETAILED DESCRIPTION OF THE INVENTION

The present invention is broadly applicable to all types of dental devices including veneer crowns, full crowns, copings, pontics, inlays, onlays, or bridges. Instances which illustrate the invention are single copings with one abutment and three-tooth bridges with two abutments and one pontic, but these are merely illustrative, not limiting.

The advantages to the dental profession and the patient of the present invention, compared to casting by the investment or "lost wax" process, are: high degree of dimensional control for copings and other fixed prosthodontic devices, lower alloy consumption per unit, less labor per unit, shorter processing time, lower porosity parts, stronger parts, reduction in time for receiving the impression to returning the prosthodontic device, and a simpler manual technique.

In analyzing relative expansion of ceramic die materials and dental alloys, one first must diferentiate between physical expansion and thermal expansion. Physical expansion is an irreversible change based on change in structure, such as heating kyanite to form mullite, or causing magnesium oxide to react with monoammonium phosphate. Such structural change creates a one-time expansion at a definitive temperature or occurrence.

Figure 1:
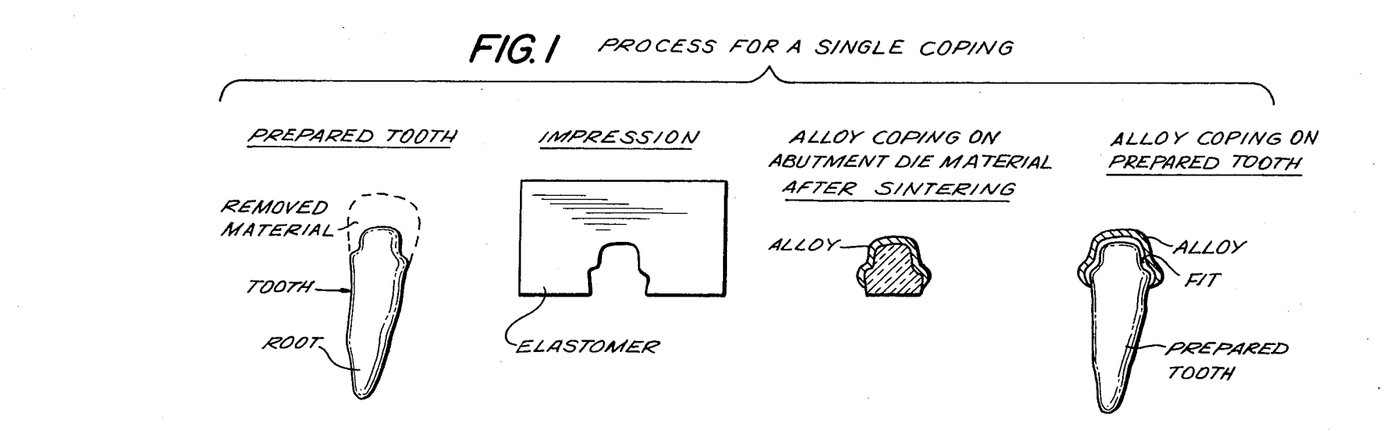
FIG. 1 shows the steps of the process of the present invention for making e.g. a single coping.
Figure 3:
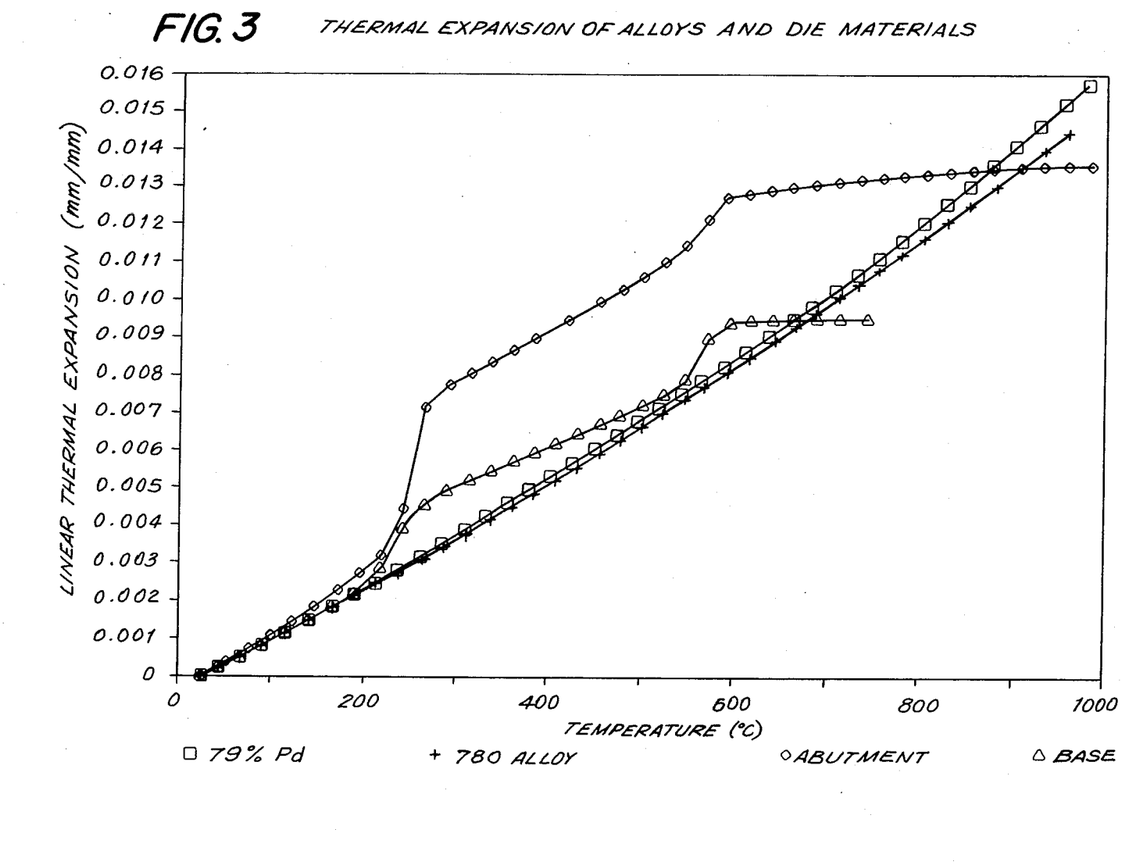
FIG. 3 shows the linear thermal expansion plotted against temperature for (a) an abutment die material, (b) a base die material, (c) a nickel-boron-silicon alloy, and (d) an 80% palladium alloy.

Thermal expansion is reversible. When a material heats up, it expands. When that material cools, it contracts, as shown in FIG. 3. The essence of building a good "fit" into a siliceous die material/dental alloy combination is that the die material has enough one-time physical expansion, so that when the coping on the die model cools down, the coping is larger than the prepared tooth surface, as shown in FIG. 1. Thus, the coping will be at least 20 microns larger than the model of the prepared tooth. This 20-30 micron increase enables the dentist or technician to get the sintered coping onto the prepared tooth, and provides the proper room for an adhesive holding the coping on the prepared tooth, as shown in Table 1. Ideally this space is less than 50 microns.

TABLE 1

| Inner Diameter of Sintered Crowns and Their Fit | | | | |
|---|---|---|---|---|
| % Physical | Outer Diameter of Prepared Tooth | | | |
| Expansion Die Material | 3 mm 3000 mu | 4 mm 4000 mu | 5 mm 5000 mu | 6 mm 6000 mu |
| −2 | 2940 mu/ −30 mu | 3920 mu/ −40 mu | 4900 mu/ −50 mu | 5880 mu/ −60 mu |
| −1 | 2970/−15 | 3960/−20 | 4950/−25 | 5940/−30 |
| 0 | 3000/0 | 4000/0 | 5000/0 | 6000/0 |
| +1 | 3030/+15 | 4040/+20 | 5050/+25 | 6060/+30 |
| +2 | 3060/+30 | 4080/+40 | 5100/+50 | 6120/+60 |
| +3 | 3090/+45 | 4120/+60 | 5150/+75 | 6180/+90 |

Only if there is a positive physical expansion of the ceramic will the final sintered alloy restoration be placeable onto the prepared tooth. If the "expansion" of the die material is negative (it actually contracts) or zero, it will not be possible to fit the coping onto the prepared tooth. That is negative fit in Table 1.

Figure 4:
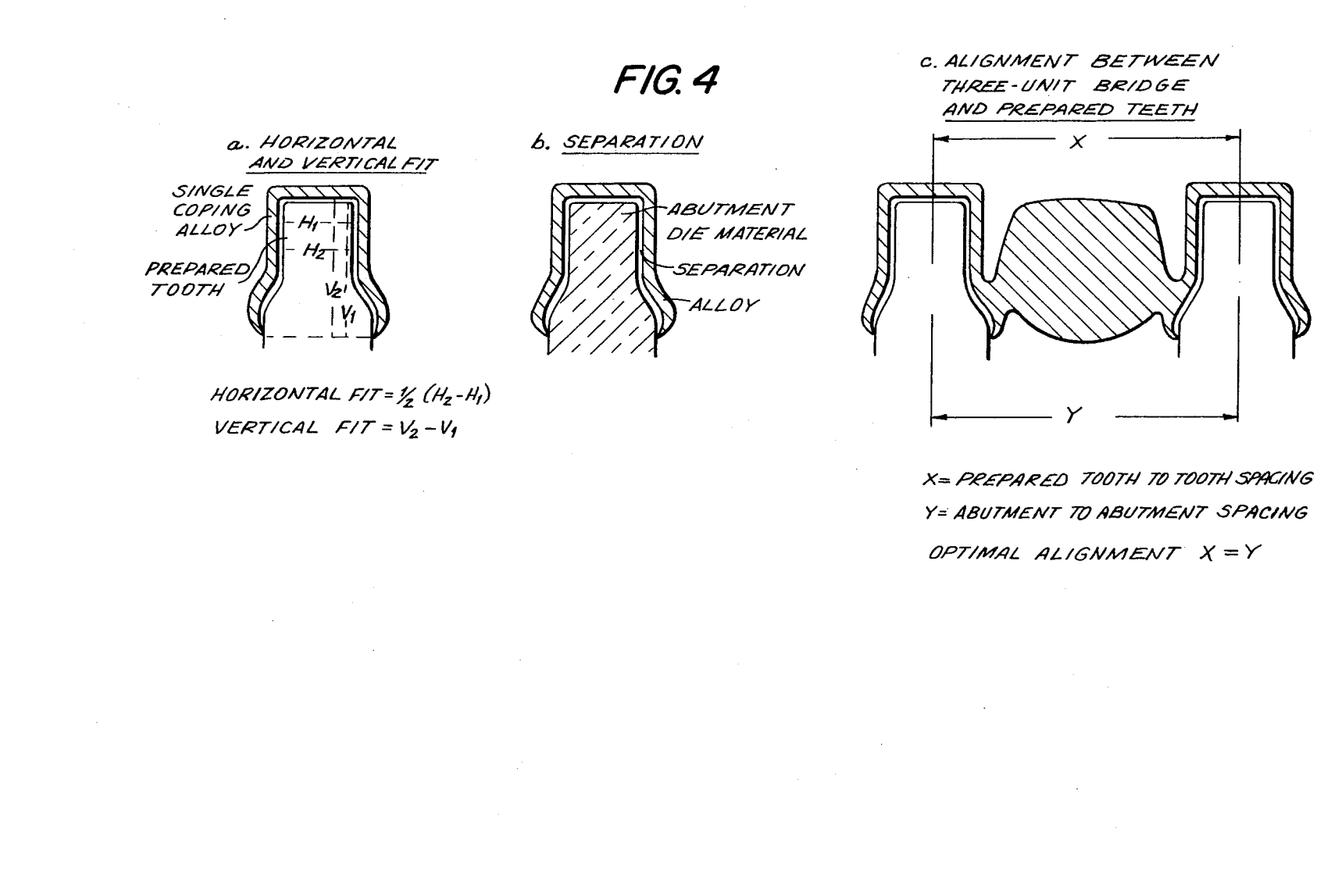
FIG. 4 shows in diagrammatic form the quality of "fit", for a coping as measured both by height and by diameter of the prepared tooth, as well as "separation" and "alignment".

"Horizontal fit" is defined as half the difference between the inner diameter of a liquid-phase sintered alloy coping and the outer diameter of the prepared tooth and shown for idealized teeth of 3-6 mm. in Table 1. The "vertical fit" is defined as the difference between the height of a sintered metal coping and that of an idealized tooth as shown in FIG. 4.

"Separation" relates to the ability to remove the sintered alloy coping from the ceramic replication without destroying the latter.

"Separation" depends on the thermal expansion of an abutment die material minus the thermal expansion of the sintered alloy coping, both shown in FIG. 3 at some intermediate treating temperature. The essence of the present invention is that this difference be positive, as illustrated in Table 2. "Separation" is defined as the space between the inner surface of the sintered alloy coping and the outer surface of an abutment die material at ambient temperature, normally 2 to 25 microns.

TABLE 2

Diameter of Copings Compared To Die Models And Corresponding Separation

| Differential Thermal Expansion (mm/mm) Die Material- Sintered Alloy | Outer Diameter of Die Model Prepared Tooth | | | |
|---|---|---|---|---|
| | 3 mm 3000 mu | 4 mm 4000 mu | 5 mm 5000 mu | 6 mm 6000 mu |
| +0.005* | 3015/ +7.5 mu | 4020/ +10 | 5025/+12.5 | 6030/+15 |
| 0 | 3000/0 | 4000/0 | 5000/0 | 6000/0 |
| −0.005@ | 2985/ −7.5 mu | 3980/ −10 | 4975/−12.5 | 5970/−15 |

*This invention, coping separates from die model
@Tension, separation of coping from die model not possible For separation to be achieved the abutment die material must have a larger thermal expansion between treatment temperature and the ambient temperature than the sinterable alloy. As shown in FIG. 3, below 900° C. the abutment die material has a larger thermal expansion than does a dental alloy. At about 900° C. the ceramic die material and the dental alloy have an equal thermal expansion. Above 900° C. the thermal expansion of a dental alloy continues to increase linearly, but the thermal expansion of the ceramic die material remains almost constant. For the proper practice of this invention the differential expansion (vertical distance between the expansion curves) below about 900° C., where the thermal expansion of the die material is greater than that of the dental alloy, must be greater than that above 900° C. where the thermal expansion of the dental alloy is greater. There is a post-sintering "treatment" to relieve stress at about 600° C. to 900° C. wherein "creep" takes place. Because of differential thermal expansion separation occurs on cooling, as shown in Table 3. Although it is not recommended, this invention can be practiced by a slow cooling from a high sintering temperature to ambient temperature by merely cutting off power to an electric oven, thus allowing the work to cool slowly and evenly. Table 3 shows the effect on separation by increasing the heat treatment temperature from 600° C. to 900° C. for the palladium alloy and abutment die material of FIG. 3.

TABLE 3

| Effect of Heat Treatment Temperature on Separation | | | | |
|---|---|---|---|---|
| Differential Thermal Expansion, Die Material- Alloy (mm/mm) | Outer Diameter of Abutment Die Material | | | |
| | 3 mm | 4 mm | 5 mm | 6 mm |
| 600° +0.0048 | 7.3 mu | 9.8 mu | 12.1 mu | 14.5 mu |
| 700° +0.0035 | 5.3 | 7.1 | 8.8 | 10.6 |
| 800° +0.0019 | 2.9 | 3.8 | 4.8 | 5.8 |
| 900° +0.0003 | 0.5 | 0.6 | 0.8 | 0.9 |

Figure 2:
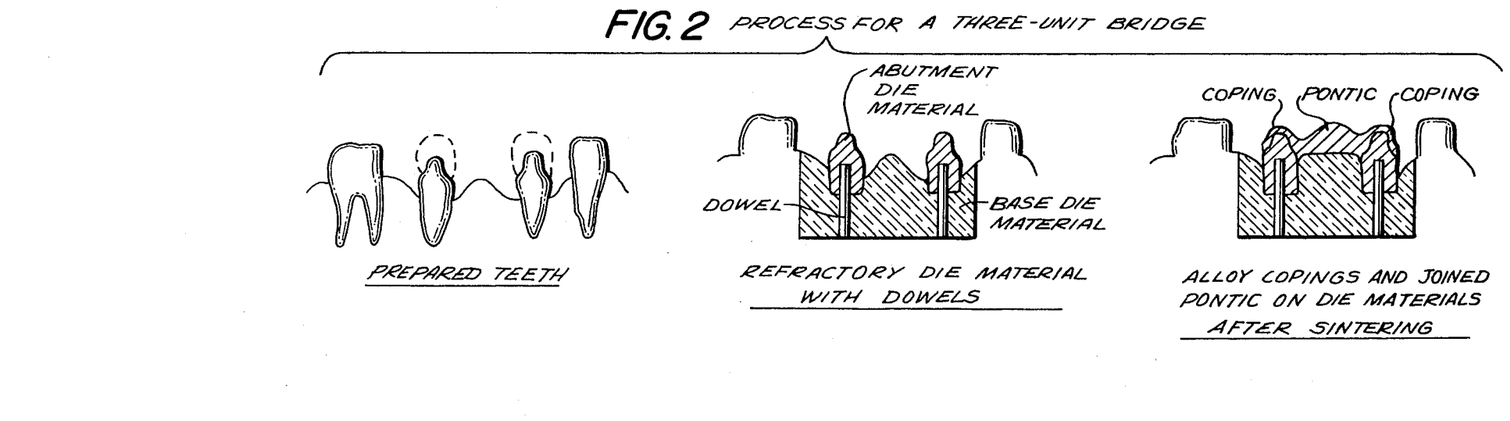
FIG. 2 shows the steps of the process of the present invention for making a three-unit bridge.

In the making of a multitooth dental device of the present invention two die materials are preferred, as shown in FIG. 2. These two materials have different thermal expansions, as shown in FIG. 3. The abutment die material must have a larger thermal expansion than that of the dental alloy so that there is good "separation" and a positive physical expansion so that there is good "fit". The base die material must have about the same overall thermal expansion as that of the dental alloy in the processing range of temperature so that there is good "alignment" and hence good "seating" of the finished dental device in the patient's mouth, as well as essentially zero physical expansion. It is an important aspect of the present invention that two different die materials with different thermal expansions be employed for the reason given. They have entirely separate functions, hence must have entirely different thermal expansions.

The process of the present invention comprises the following steps:

(a) An impression of the dental surface is formed using a conventional elastomeric material such as polysulfide or silicone.

(b) A siliceous abutment die material is mixed having a thermal expansion and a physical expansion so interrelated with the thermal expansion of the alloy to be used that the eventual alloy coping is slightly larger than the prepared the tooth or teeth (proper fit and separation). Preferably "slightly larger" means from about 25 to about 40 microns larger; below 50 microns is greatly favored. By thermal expansion we mean the reversible expansion of most materials when heated, often termed the linear thermal expansion. Upon cooling the material returns to its original size. By physical expansion we mean the irreversible expansion of a material which occurs upon a change in physical form, such as the change of kyanite to mullite; or a chemical reaction, such as ammonium phosphate plus magnesium oxide to give magnesium ammonium phosphate. For a single tooth, only an abutment die material is necessary, since only a single coping is to be made. The combined physical and thermal expansion of an abutment die material should be substantial so that the alloy coping is larger that the prepared tooth, as shown in FIG. 1.

For a multi-tooth device such as a three-unit bridge, two die materials are necessary; the abutment die material and a base die material, as shown in FIG. 2. The role of the base die material is to be a stable matrix keeping two or more abutments separated at a desired distance throughout the process. Therefore the expansion coefficient of the base die material should be low, as shown in FIG. 3.

(c) The next step is to fill the dental impression of step (a) with the abutment die material or abutment/base combination of die materials to create the die preform. Optionally at this point one or more pins are inserted in the raw die material to make handling of the dental device easier, later. Alumina is the favored material for the pins (dowels).

(d) The die preform is then separated from the dental impression. If an undercut is noted, it may be filled in with additional abutment die material. Likewise a spacer may be used.

(e) The solid die preform is then fired at a temperature below 1500° C.; about 1300° C. is preferred. This firing causes gases and vapors to be removed with concomitant strengthening of the die material.

(f) The surface of the die material is first metallized with high melting fine, metallic particles then covered in one or more layers of lower melting powdered metal alloy, as shown in FIG. 2. A wide variety of alloys may be employed such as titanium alloys, nickel-chromium, nickel-boron-silicon, chromium-cobalt, silver-palladium, gold-palladium, any high gold alloy, and any high palladium alloy (about 80% or more). A high palladium (50-95%) or titanium alloy is preferred. The alloy is chosen in the present invention for its expansion coefficient, as also shown in FIG. 3. The interrelation of the alloy in the present invention with the properties of the abutment die material and the base die material (for two or more abutments), achieve the goal of the present invention: namely dental devices which are slightly larger than the ceramic replicas on which they are based, preferably less than 2-25 microns larger.

(g) The powdered metal alloy is then sintered between a temperature of 900° C. and 1400° C. to form the dental device.

One of the siliceous components of the die materials is alpha-quartz, which has a high thermal coefficient of expansion. It is essentially pure silica, over 99.5% with small amounts of alumina, iron oxide, and titania in that order plus trace amounts of calcium oxide and magnesium oxide. Preferably most of the quartz particles should pass through a screen of 200 mesh (74 microns); in fact about half of suitable commercial alpha-quartz is less than 20 microns. A suitable commercial source is Sil-Co-Sil 295 from the Ottawa Silica Co. of Ottawa, Ill. In abutment die materials the usual amount of alpha-quartz ranges from 50% to 95%. In base die material the usual amount is lower (about 30% to 75%) but compensated by a component with lower thermal expansion such as zircon. Alpha-quartz has a thermal expansion of about 1.4% above 600° C. At 573° C. it transforms to beta quartz.

Another material, almost pure silica, which may be used interchangeably or in combination with alpha quartz, is alpha-cristobalite, which at about 200° C. is transformed to beta-cristobalite. The beta-form has a high thermal expansion rising steadily from about 1.2% at 200° C. to about 1.5% at 1000° C. In the abutment die material from about 5% up to 50% is preferred; in the base die material from about 5% up to about 40%. Alpha-cristobalite is commercially available from the CED Process Minerals Co. of Cuyahoga Falls, Ohio in the form of a minus 200 mesh (74 microns) powder, over half of which is less than 20 microns. Minus 325 mesh (44 microns) and minus 400 mesh (38 microns) are also suitable and commercially available. Fused silica (from about 10% up to about 40% of the total) may also be employed; it has a thermal expansion of about 0.1 percent between ambient and 1000° C. In order to lower the thermal expansion of the silica component of an abutment or base die material one may use zircon, in the form of a minus 200 mesh (74 microns) powder. This has a thermal expansion of only about 0.4% between ambient and 1000° C. Zircon, zirconium silicate, is available from M & T Chemical Co., Rahway, N.J.

To practice this invention the physical expansion of an abutment die material should be about zero to about 3% and its thermal expansion should be greater than that of the sinterable alloy used (good separation). Since the role of the base die material is to maintain a desirable distance between abutments (see FIG. 2), it should have a physical expansion approximately zero and a thermal expansion approximately that of the sinterable alloy at about 600° C.-900° C. (0.004-0.015 mm/mm).

The particle size of alpha-quartz employed is less than about 90 microns; that of alpha-cristobalite is less than about 90 microns. The colloidal silica suspensions have a particle size from about 50 to 250 angstroms.

There are at least two means for achieving physical expansion: (a) employing a siliceous material which undergoes a transformation such as kyanite to mullite, or (b) utilizing a chemical reaction of the binder components to change the particulate silica to a uniform ceramic, e.g. the reaction which makes magnesium ammonium phosphate with a physical expansion of about 2%.

A siliceous refractory die material is set within a few minutes by mixing the silica with a binder. A preferred binder is a mixture of magnesium oxide (5-40% of the total), a suspension of colloidal silica (10-40%) and ammonium dihydrogen phosphate (5-40%). Other polyvalent oxides may be employed to react with the colloidal silica, which itself might be replaced by ethyl silicate or other siliceous liquids in amounts from about 10% to 50%. The ammonium phosphate acts both as a buffering agent and as a soluble reactant for the polyvalent cation. The chemical reaction of the setting reaction should take place within about five minutes. This reaction not only provides the necessary expansion for the finished die to be slightly larger than the original tooth but also gives the die material its "green" strength. The concentration of colloidal silica may vary from abaout 5% to about 60%.

The die material is allowed to remain in the impression mould to finish the setting reactions for about one-half to one hour before being removed from the mould and fired. While the die material is still soft one or more dowels or pins may be positioned in the refractory mould, depending on the number of teeth being modeled. Alumina is the preferred material for the dowels.

A representative formulation for an abutment die material is 13.6 parts alpha-quartz, 2.4 parts alpha-cristobalite, 2.0 parts magnesium oxide, 2.0 parts monoammonium phosphate (all powders), plus about 5 parts aqueous undiluted 40% Ludox HS40 colloidal silica suspension (duPont Co., Wilmington, Del.). Volumetrically, the desired ratio is 1.2 volumes Ludox suspension per five parts powders (24 ml/100 g). When cured for about 45 minutes and fired at about 1300° C. for 10 minutes, this formulation showed a physical expansion of about 2.5%, a thermal expansion at 600° C. of 1.2%, a working time of about five minutes, and a flexural strength of about 16.5 MPa. Another embodiment may comprise up to 40% zircon.

A representative formulation for a base die material is about 100 parts alpha-quartz, about 20 parts alpha-cristobalite, 15 parts magnesium oxide, 15 parts monoammonium phosphate, 50 parts zircon, and 50 parts 40% colloidal silica aqueous suspension (diluted HS40, duPont). When cured for about one hour and fired at 1300° C. for 10 minutes, the base die material showed a thermal expansion of 0.01 mm/mm at 700° C. and a physical expansion of about zero. The flexural strength of the fired base die was about 11 MPa.

The refractory die material may be fired at a temperature range of 900° to 1500° C. The preferred temperature is about 1300° C.

As for separation, the essence of the present invention is for there to be a positive differential thermal expansion, so that for the outer diameter of die material at room temperature in the range of 3–6 mm, the diameter of the corresponding sintered alloy coping would be about (@ +0.006 mm/mm expansion) 3018, 4024, 5030, and 6036 mu respectively. As for horizontal fit, at least 15–20 mu is preferable, so that there is room between the prepared tooth and the sintered alloy coping for a thin layer of cement of the conventional zinc phosphate or ionomer type.

In order to get good fit between a device made from an alloy sintered on a refractory die material, it is advantageous for the sintering alloy (liquid) to wet the die material, that is have a contact angle less than 90°, when contact angle is determined by Young's equation. If the sintering alloy has a high contact angle, does not wet the refractory die material, rounded and inaccurate margins may be formed. Also it is more likely for the sintering metal to crack upon shrinking without wetting.

To insure that the wetting angle is low, it is advantageous to metallize the refractory die replica with an extremely thin layer of metal about 25 microns (about 8 to about 40 mu) thick. One method of metallizing a palladium/silver alloy is to paint it on either fired or unfired refractory die material. Air firing a painted layer on unfired die material saves one step, since the firing performs two functions. Coprecipitated powders with a particulate size of about one micron are suitable. The powder may be dispersed in hydrocarbon thinner. It is preferred to fire the thin metallizing layer between the solidus and liquidus temperature of the alloy. For 60% palladium/40% silver alloys that is about 1350° C. This must be done carefully because the refractory die material is subject to cracking above 1300° C. High gold/palladium alloys e.g. 80–85% gold can be fired for metallizing at about 1200°–1300° C. After firing, the metallizing layer is from about 2 to about 8 microns thick.

Other metallizing processes such as plating, vapor deposition, sputtering, flame spraying, and the like may also be used to ensure a low contact angle between the alloy to be sintered and the refractory die material.

The product of the present invention being a liquid phase sintered dental prosthetic device has a totally different microstructure and hence different properties than the cast dental devices of the prior art. Dental alloys made up of more than one metal, following Gibbs' phase rule, will have a solidus temperature and a liquidus temperature based on the well-known "rabbit-ears" phase diagram of most alloys. The sintering process takes place for many of the dental alloys disclosed above in the temperature range of 1000° C.–1300° C. because in this range two phases are found simultaneously; a liquidus phase, rich in the low-melting component of the alloy, and a solidus phase, rich in the high-melting component of the alloy. Therefore, even though one starts with only one alloy, but more than one can be employed if desired, there are two components to the microstructure in the form of a composite. For more than one alloy there may be a plurality of discontinuous granules. The composite microstructure of discontinuous rather large grains in a continuous matrix is less porous than the uniformly granular one-phase microstructure of a cast dental device of the prior art.

Looking at a prepared cross-section in a microscope immediately informs the viewer whether or not this invention has been employed in making such a device, even though without magnification the two types of crowns, copings, or bridges appear to be identical.

Dental prosthetic devices of the present invention are characterized by two or more phases depending on the number of materials in the alloy. These are isolated grains, normally well-rounded and sized from about 20 to about 80 micrometers averaging about 50 microns. The continuous phase exhibits essentially no pores, less than 0.5 percent. The few pores are isolated and spherical in the range of less than about ten microns in size.

Cast dental prosthetic devices of the prior art have a completely different microstructure and porosity than the liquid-phase, sintered devices of the present invention. The cast pieces (Amer. Dental Assoc. spec. 38) have a fine grained structure with grains less than 50 microns in one or more phases. There is essentially no continuous matrix and the fine grains are patterned in larger domains, not isolated. Furthermore, cast structures have porosity, generally irregular. There may even be visible channels. If there are spherical pores, they are usually very small—about one micron.

FURTHER DESCRIPTION OF THE DRAWINGS

FIG. 1 illustrates the process for making a single coping. In the first of four panels the dentist prepares the tooth mostly by removing unwanted material to form a supporting abutment. In the second panel taking the impression of the prepared tooth is shown. The third panel shows a liquid-sintered alloy coping on the preformed abutment die material made from the impression. The fourth panel shows the alloy coping, separated from the abutment die material of panel three, on the prepared tooth with the distance of the fit illustrated. The space of the fit will later be infused with dental cement.

FIG. 2 illustrates the process for making a three-unit bridge. The first panel shows the prepared teeth. Two of them have abutments resulting from removed dental material. The second panel shows a preform comprising abutment die material, base die material between and under the abutments, and alumina dowels inserted in the abutments. The third panel shows a sintered alloy three-unit bridge consisting of alloy coping joined by an alloy pontic on the refractory die after sintering and before separation.

FIG. 3 gives data on the linear thermal expansion of two die materials and two alloys between ambient room temperature and 1000° C. The two alloys have monotonically increasing linear thermal expansion with arcuate data. The abutment die material shows a marked increase in thermal expansion at about 250° C. and another at about 575° C., at which point the expansion becomes negligible with increasing temperature. The base die material has lesser increases of expansion at the two transition temperatures and a constant value above 600° C. The vertical difference between the alloy and abutment die material expansion provides separation. The match of the base die material and the alloy between approximately 700° C. and ambient ensures proper alignment of multispan units.

FIG. 4 provides the quantitative basis for defining fit, separation, and alignment. In panel a. horizontal and vertical fit are graphically illustrated. Separation between the abutment die material and a sintered alloy coping is shown in panel b. Panel c. shows the identity between tooth spacings in a properly aligned bridge.

Having described the present invention above, we now illustrate it in the following Examples. These Examples, however, are intended only to illustrate not limit the instant invention, which may be carried out by other means yet still remain within the scope of this disclosure.

EXAMPLE 1

This Example illustrates the use of the present invention to make a single crown coping fitted to less than 50 microns on a prepared tooth and then layer it with dental porcelain.

A prepared posterior tooth about 6 mm in diameter and 4 mm long in the shape of a truncated cone was prepared to accept a single crown. A replica of the prepared tooth was taken using conventional dental elastomer, and the impression was prepared to accept a ceramic die material.

Separately a powder was mixed consisting of 13.6 g. alpha-quartz, 2.4 g. alpha-cristobalite, 2 g. magnesium oxide and 2 g. monoammonium phosphate; 4.8 ml 40 percent Ludox HS 40 brand colloidal silica (duPont Co.) liquid was then stirred in to make an abutment die material of uniform consistency with a working time of about five minutes.

The abutment die material was vibrated into the impression of the prepared tooth; an alumina holding pin was set into the viscous ceramic; and then it was allowed to set and cure.

After one hour the cured abutment die material was taken out of the impression. It showed a physical expansion of 1.0 percent and a thermal expansion of 0.0135 mm/mm between ambient and 700° C. The model tooth was then fired at 1350° C. for ten minutes in air.

The fired model was then coated with fine metallizing powder less than five microns of 60/40 palladium/silver alloy in Adsol thinner (Alloy Metals Inc., Troy, Mich.) to give a smooth, uniform coating about 20-30 mu thick. The coated model was then heated another ten minutes at 1350° C. in air to give an applied layer about 5 mu thick.

A sinterable alloy mixture was then prepared from 79 percent palladium, 10 percent copper, 9 percent gallium, and 2 percent gold and 2 percent (Adsol cement 1260) diluted to a paintable consistency with Adsol thinner. A die model was coated to a thickness of about 0.3-0.5 mm and then allowed to air dry. After drying, the die model coated with sinterable alloy was placed in a vacuum furnace at 350° C., which was then evacuated to about 50 millitorr. The following sintering cycle under vacuum was then carried out: 1165° C. (2 min.); 750° C. (10 min.); then removed at 550° C. The thermal expansion from ambient to 700° C. of the sinterable alloy is 0.0095 mm/mm. The differential thermal expansion between the abutment die material and the sinterable alloy between ambient and 700° C. is 0.004 mm/mm. The coping was separated.

The alloy coping was touched up with additional sintering alloy powder and refired in the same cycle as above. Prior to adding porcelain the alloy coping is heat treated to oxidize its surface in air at 980° C. for five minutes. The die continued to serve as a support, however, after separation.

In the conventional manner, according to the usual instructions opaque dental porcelain was applied and fired in two layers. Then conventional gingival and incisal dental porcelains were applied. Then the coping of this Example was seated onto the prepared tooth.

This coping exhibited the usual microstructure of a liquid sintered metal: isolated, rounded grains in a continuous matrix with a low porosity of about 0.5 percent. The individual pores were isolated and spherical less than ten microns in diameter.

The cement gap or final "fit" of this coping was 42 microns. The porcelain bonded well. There were no signs of cracking or checking.

EXAMPLES 2, 3, AND 4

These Examples illustrate the effect of preparation diameter, physical expansion of abutment die material, and differential thermal expansion between the abutment die material and the liquid-phase sinterable alloy powder on the final fit and separation of crown copings for individual posterior teeth whose prepared diameter was 6 mm.

The same procedure was employed as in Example 1 with the following results:

| Example | Physical Expansion % | Differential Thermal Expansion at the Heat Treatment Temperature mm/mm | Final Fit mu |
| --- | --- | --- | --- |
| 2 | 1.0 | 0.002 | 36 |
| 3 | 1.5 | 0.002 | 51 |
| 4 | 1.5 | 0.004 | 57 |

EXAMPLE 5

This Example illustrates the application of the present invention for making a single crown of an anterior tooth. The procedure of Example 1 was used.

The prepared anterior tooth was 3 mm in diameter and 5 mm high. The abutment die material showed 2.0 percent physical expansion and 0.0135 mm/mm thermal expansion.

A final fit of 36 mu was achieved.

EXAMPLES 6, 7, 8

These Examples illustrate the effect of preparation diameter, physical expansion, differential thermal expansion, and heat treatment temperature on final fit and separation of single crowns for anterior teeth having a prepared diameter of 3 mm.

The same procedures were employed as in Example 5, with the following results:

| Example | Physical Expansion of Abutment Die (%) | Expansion at Heat Treatment Temperature mm/mm | Final Fit (microns) |
| --- | --- | --- | --- |
| 6 | 2.0 | 0.002 | 33 |
| 7 | 2.5 | 0.002 | 41 |
| 8 | 2.5 | 0.004 | 44 |

EXAMPLE 9

This Example illustrates the use of palladium as a metallizing alloy.

The same procedure as in Example 1 was employed except that a 70/30 palladium/silver metallizing alloy powder was used. The firing temperature was increased to 1400° C., between the liquidus and solidus temperatures of this alloy.

The same results as in Example 1 were achieved with this alloy.

EXAMPLE 10

This Example illustrates the use of a lower melting sinterable alloy 92.7 percent Ni/2.8 B/4.5 Si, dental alloy 780, Alloy Metals Inc. Troy, Mich., to prepare a single crown. Because the lower melting alloy was used, the sintering temperature was decreased.

The procedure of Example 1 was used except that the firing step was accomplished at 1020° C. for ten minutes. No precoat metallization step was necessary.

EXAMPLE 11

This Example illustrates the elimination of the heat treatment step at about 700° C.

The procedure of Example 1 was employed except that after sintering the vacuum oven assembly was alloyed to cool slowly from the sintering temperature to about 550° C., whereupon the work was removed from the oven.

The separation and fit were normal, as in Example 1.

EXAMPLE 12

This Example illustrates the use of the present invention to make a three-unit bridge. Two posterior teeth with a tooth missing between them were prepared in such a way that the three spaces would take a three-unit bridge consisting of two abutments and one pontic.

The dimensions of the two abutments were similar to the prepared tooth of Example 1. The overall length of the bridge was about 25 mm.

An impression of the quadrant involved was made in the conventional fashion.

Two die materials were employed. The high expanding abutment die material of the present invention and the merely compensating expansion die material for the base. As in Example 1, the abutment die material was made, poured, alumina pins inserted, and allowed to set and cure. This abutment die material showed a physical expansion of 1.0 percent and thermal expansion between ambient and 700° C. of 0.0135 mm/mm.

After a cure of one hour, the exposed surfaces were covered with nitrocellulose film which would burn out at firing temperature. Then the base die material was prepared, as above, and poured into the remaining parts of the dental impression to join the abutments, as shown in FIG. 2. The base die material showed a physical expansion of zero and a thermal expansion from ambient to 700° C. of 0.0095 mm/mm.

After an hour set and cure, the entire bridge die assembly was removed from the impression and fired at 1350° C. for ten minutes in air.

The surface of the bridge was then metallized, as in Example 9.

Employing a liquid-sinterable alloy powder (minus 120 mesh) of 79 percent palladium/10 percent copper/9 percent gallium/2 percent gold the two abutments were individually built up and fired, as described in Example 1. In the second stage the sinterable alloy was used to sculp a pontic as shown in FIG. 2. The complete assembly was fired, touched up. refired, and porcelainized as in Example 1.

This bridge was accurately seated onto the prepared teeth.

Having illustrated, but not limited, some aspects of the present invention by the Examples above, the scope of protection sought to be granted by Letters Patent is more fully described in the following claims. It will be obvious to those skilled in the art that other high precision, biomechanical devices requiring tolerances of a few micrometers may be produced by the same techniques as those disclosed and exemplified above. These orthopedic devices are exemplified by reconstructive parts, bone pins, or other biomechanical fasteners.

We claim:

1. A dental article comprising a dental prosthetic device being a liquid-phase sinterable metallic alloy, characterized by a multiphase, composite microstructure of isolated spherical grains approximately 50 microns in diameter distributed in an essentially nonporous matrix.

2. The dental prosthetic device of claim 1, wherein the device is a full cast crown, a coping, a pontic, an inlay, an onlay, or a bridge.

3. The dental prosthetic device of claim 1, wherein the alloy is chosen from the group consisting of nickel-chromium, gold-palladium chromium-cobalt, a high gold alloy, a high palladium alloy, a silver-palladium alloy, a nickel-boron-silicon alloy, and a titanium alloy.

4. A dental assembly comprising in combination:
   (a) a dental prosthetic device being a liquid sinterable, metallic alloy portion characterized by a multiphase composite microstructure of isolated spherical grains approximately 50 microns in diameter distributed in an essentially nonporous matrix; and
   (b) a siliceous die material portion characterized by a thermal expansion between ambient and 600° C. between about 0.008 mm/mm and about 0.015 mm/mm and a physical expansion between zero and 0.03 mm/mm,
      whereby the dental surface of the die material portion is removable from the alloy portion with a separation of about 2 to about 25 micrometers.

5. An assembly as in claim 4, wherein the fit between the alloy portion and a prepared tooth is from about 10 microns to about 75 microns.

6. The assembly of claim 4 wherein the device is a full cast crown, a veneer crown, a coping, an inlay or an onlay.

7. A dental assembly comprising in combination:
   (a) a multitooth dental prosthetic device being a liquid sinterable, metallic alloy portion characterized by a multiphase composite microstructure of isolated spherical grains approximately 50 microns in diameter distributed in an essentially nonporous matrix; and
   (b) a siliceous die material portion having abutments characterized by a thermal expansion between ambient and 600° C. between about 0.008 mm/mm and about 0.015 mm/mm and a physical expansion between zero and 0.03 mm/mm, and having a base die material characterized by a thermal expansion between ambient and 600° C. between about 0.004 mm/mm and about 0.015 mm/mm and a physical expansion approximately zero,
      whereby the dental surface of the die material portion is separable from the abutments of the alloy portion with a separation of from about 2 to about 25 microns.

8. The assembly of claim 7, wherein the fit between the abutments of the alloy portion and the prepared teeth is from about 10 microns to about 75 microns and the abutments are well aligned.

9. A method for fabricating a single coping dental prosthetic device comprising the steps of:
(a) forming an impression of the prepared dental surface;
(b) mixing a siliceous abutment die material having a thermal expansion between ambient and 600° C. greater than 0.008 mm/mm and a physical expansion between zero and 0.03 mm/mm;
(c) filling the impression with the abutment die material to form a die preform;
(d) separating the preform from the impression;
(e) firing the abutment die material at a temperature below 1500° C.
(f) covering the die material with a powdered metal alloy having an expansion between ambient and 600° C. between 0.004 mm/mm and 0.015 mm/mm;
(g) firing the alloy composite under vacuum at a temperature between 900° C. and 1400° C. to form a single coping of the single crown by sintering;
whereby the separation between the die and the alloy is from about 2 to about 25 microns.

10. An alloy coping for a single crown made by the method of claim 9.

11. The method of claim 9 wherein the alloy is selected from the group consisting of nickel-chromium, gold-palladium, silver-palladium, chromium cobalt, a high gold alloy, a high palladium alloy, a nickel-boron-silicon alloy, and an alloy of titanium.

12. The method of claim 11, wherein the palladium content of the alloy is between 50% to 95%.

13. The method of claim 11, wherein the palladium content of the alloy is between 79% and 95%.

14. The method of claim 9 wherein the abutment die material comprises 50% to 95% alpha-quartz, up to 50% alpha-cristobalite, up to 40% zircon 5% to 40% magnesium oxide, 5% to 40% monoammonium phosphate, and up to 40% colloidal silica suspension.

15. The method of claim 9 wherein the pressure of step (g) is between 10 and 100 millitorr.

16. The method of claim 9, wherein the siliceous abutment die material of step (b) contains from 10% to 50% ethyl silicate.

17. The method of claim 9, wherein the preform of step (d) contains at least one alumina dowel.

18. A method as in claim 9, further comprising a step (e') between steps (e) and (f) as follows:
(e') metallizing the die material with a high melting fine powder.

19. A method as in claim 18, wherein the metallizing layer is about 8–40 microns thick before firing and about 2-8 microns thick after firing.

20. An alloy coping for a single crown made by the method of claim 18.

21. A method of fabricating a multitooth dental prosthetic device comprising the steps of:
(a) forming an impression of a multitooth dental surface comprising a base with abutments;
(b) mixing separately a siliceous base die material having a thermal expansion between ambient and 600° C. between 0.004 mm/mm and 0.015 mm/mm and a physical expansion approximately zero and a siliceous abutment die material having a thermal expansion between ambient and 600° C. between 0.008 mm/mm and 0.015 mm/mm and a physical expansion between zero and 0.03 mm/mm;
(c) filling the base of the multitooth impression with the base die material and the abutments of the multitooth impression with the abutment die material to form a multitooth die preform with at least one base and a least two abutments;
(d) separating the multitooth preform from the impression;
(e) firing the die material at a temperature below 1500° C. to form a solid die having a preform of the multitooth surface;
(f) covering the preform of the surface with a powdered metal alloy having an expansion between ambient and 600° C. between 0.004 mm/mm and 0.015 mm/mm to form copings on the abutment die areas and a pontic on the base die area;
(g) firing the alloy preform composite under vacuum at a temperature between 900° C. and 1400° C. to form a bridge by sintering;
whereby the separation between the alloy bridge and the preform of the dental surface is from about 2 to about 25 microns.

22. The method of claim 21 wherein the base die material comprises 30% to 75% alpha-quartz, up to 40% alpha-cristobalite, up to 40% zircon, 5% to 40% magnesium oxide, 5% to 40% monoammonium phosphate, and up to 40% colloidal silica suspension.

23. The method of claim 21 wherein the pressure of step (g) is between 10 and 100 millitorr.

24. The method of claim 21, wherein the siliceous base die material of step (b) contains from 10% to 50% ethyl silicate.

25. The method of claim 21, wherein the multitooth preform of step (d) contains at least one alumina dowel.

26. A method as in claim 21, further comprising a step (e') between steps (e) and (f) as follows:
(e') metallizing the die material with a high-melting fine powder.

27. A method as in claim 26, wherein the metallizing layer is about 8-40 microns thick before firing and about 2-8 microns thick after firing.

28. An alloy bridge made by the method of claim 26.

29. A multitooth dental prosthetic device made by the method of claim 21.

30. A biomechanical article comprising a biomechanical device being a liquid-phase sinterable metallic alloy, characterized by a multiphase, composite microstructure of isolated spherical grains approximately 50 microns in diameter distributed in an essentially nonporous matrix.

31. A biomechanical device of claim 30, wherein the alloy is chosen from the group consisting of nickel-chromium, gold-palladium, chromium-cobalt, a high gold alloy, a high palladium alloy, a silver-palladium alloy, a nickel-boron-silicon alloy, and a titanium alloy.

32. A biomechanical assembly comprising in combination:
(a) a biomechanical device comprising a liquid sinterable, metallic alloy portion characterized by a multiphase composite microstructure of isolated spherical grains approximately 50 microns in diameter distributed in an essentially nonporous matrix; and
(b) a siliceous die material portion characterized by a thermal expansion between ambient and 600° C. between about 0.008 mm/mm and about 0.015 mm/mm and a physical expansion between zero and 0.03 mm/mm, whereby the surface of the die material portion is removable from the alloy portion with a separation of about 2 to about 25 micrometers.

33. An assembly as in claim 32, wherein the fit between the alloy portion and a bone surface is from about 10 microns to about 75 microns.

34. A method for fabricating a single coping biomechanical device comprising the steps of:
    (a) forming an impression of the prepared surface;
    (b) mixing a siliceous abutment die material having a thermal expansion between ambient and 600° C. greater than 0.008 mm/mm and a physical expansion between zero and 0.03 mm/mm;
    (c) filling the impression with the abutment die material to form a die preform;
    (d) separating the preform from the impression;
    (e) firing the abutment die material at a temperature below 1500° C.;
    (f) covering the die material with a powdered metal alloy having an expansion between ambient and 600° C. between 0.004 mm/mm and 0.015 mm/mm;
    (g) firing the alloy composite under vacuum at a temperature between 900° C. and 1400° C. to form a single coping of the single crown by sintering;
    whereby the separation between the die and the alloy is from about 2 to about 25 microns.

35. The method of claim 34 wherein the alloy is selected from the group consisting of nickel-chromium, gold-palladium, silver-palladium, chromium-cobalt, a high gold alloy, a high palladium alloy, a neckel-boron-silicon alloy, and an alloy of titanium.

36. A method as in claim 34, further comprising a step (e') between steps (e) and (f) as follows:
    (e') metallizing the die material with a high-melting fine powder.

37. A biomechanical article comprising a biomechanical device being a liquid-phase sinterable metallic alloy, characterized by a grain structure of grains having an average size of from about 20 microns to about 80 microns.

38. The biomechanical device of claim 37, which is a dental prosthetic device.

39. A biomechanical assembly comprising in combination:
    (a) a biomechanical device being a liquid-sinterable, metallic alloy portion characterized by a grain structure of grains having an average size of from about 20 microns to about 80 microns; and
    (b) a siliceous die material portion characterized by a thermal expansion between ambient and 600° C. between about 0.008 mm/mm and about 0.015 mm/mm and a physical expansion between zero and 0.03 mm/mm,
    whereby the dental surface of the die material portion is removable from the alloy portion with a separation of about 2 to about 25 micrometers.

40. The assembly of claim 39, wherein the biomechanical device is a dental prosthetic device.

41. A dental assembly comprising in combination:
    (a) a multitooth dental prosthetic device being a liquid sinterable, metallic alloy portion, characterized by a grain structure of grains having an average size of from about 20 microns to about 80 microns; and
    (b) a siliceous die material portion having abutments characterized by a thermal expansion between ambient and 600° C. between about 0.008 mm/mm and about 0.015 mm/mm and a physical expansion between zero and 0.03 mm/mm, and having a base die material characterized by a thermal expansion between ambient and 600° C. between about 0.004 mm/mm and about 0.015 mm/mm, and a physical expansion approximately zero,
    whereby the dental surface of the die material portion is separable from the abutments of the alloy portion with a separation of from about 2 to about 25 microns.

42. A biomechanical assembly comprising in combination:
    (a) a biomechanical device being a liquid-sinterable, metallic alloy portion characterized by a grain structure of grains having an average size of from about 20 microns to about 80 microns;
    (b) a siliceous die material portion characterized by a thermal expansion between ambient and 600° C. between about 0.008 mm/mm and about 0.015 mm/mm and a physical expansion between zero and 0.03 mm/mm; and
    (c) a metallizing layer between said metallic alloy portion and said die material;
    whereby the dental surface of the die material portion is removable from the alloy portion with a separation of about 2 to about 25 micrometers.

43. The assembly of claim 42, wherein the biomechanical device is a dental prosthetic device.

44. A dental assembly comprising in combination:
    (a) a multitooth dental prosthetic device being a liquid sinterable, metallic alloy portion, characterized by a grain structure of grains having an average size of from about 20 microns to about 80 microns;
    (b) a siliceous die material portion having abutments characterized by a thermal expansion between ambient and 600° C. between about 0.008 mm/mm and about 0.015 mm/mm and a physical expansion between zero and 0.03 mm/mm, and having a base die material characterized by a thermal expansion between ambient and 600° C. between about 0.004 mm/mm and about 0.015 mm/mm, and a physical expansion approximately zero; and
    (c) a metallizing layer between said metallic alloy portion and said die material;
    whereby the dental surface of the die material portion is separable from the abutments of the alloy portion with a separation of from about 2 to about 25 microns.

* * * * *